United States Patent

Berner et al.

[11] Patent Number: 5,676,525
[45] Date of Patent: Oct. 14, 1997

[54] VACUUM LIMITING MEDICAL PUMP

[75] Inventors: Werner Berner, Oberlinsbach; Robert Riedweg, Eich, both of Switzerland

[73] Assignee: Neovation AG, Erch, Switzerland

[21] Appl. No.: 692,669

[22] Filed: Aug. 6, 1996

Related U.S. Application Data

[63] Continuation-in-part of Ser. No. 198,825, Feb. 18, 1994, abandoned.

[30] Foreign Application Priority Data

Feb. 19, 1993 [CH] Switzerland ............ 00 533/93

[51] Int. Cl.$^6$ .................................. F04B 49/06
[52] U.S. Cl. .................................. 417/44.1
[58] Field of Search .................. 417/44.1, 44.11, 417/326, 415, 12; 604/74

[56] References Cited

U.S. PATENT DOCUMENTS

| | | | |
|---|---|---|---|
| 2,346,841 | 4/1944 | Henderson | 604/74 |
| 3,610,782 | 10/1971 | McGuire, III | 417/326 |
| 4,566,868 | 1/1986 | Menzies | 417/415 |
| 4,617,637 | 10/1986 | Chu et al. | 417/415 |
| 4,759,747 | 7/1988 | Aida et al. | 604/74 |
| 4,857,051 | 8/1989 | Larsson | 604/74 |
| 4,919,596 | 4/1990 | Slate et al. | 417/415 |
| 4,925,371 | 5/1990 | Giesmar | 417/415 |
| 4,961,726 | 10/1990 | Richter | 604/74 |
| 5,120,199 | 6/1992 | Youngs et al. | 417/18 |

FOREIGN PATENT DOCUMENTS

| | | |
|---|---|---|
| 0 330 845 | 9/1989 | European Pat. Off. . |
| 0 401 067 | 12/1990 | European Pat. Off. . |
| 38 20 211 | 11/1988 | Germany . |
| 40 31 708 | 4/1992 | Germany . |

*Primary Examiner*—Timothy Thorpe
*Assistant Examiner*—Xuan M. Thai
*Attorney, Agent, or Firm*—Helfgott & Karas, P.C.

[57] ABSTRACT

A pump having electronic and mechanical components which allow an individually adjustable operation. Certain components periodically transform a driving current for an electrical drive. An adjustable clock generator adjusts transformation frequency. Pumping volume is determined and limited as desired by means of a position detection device. The pump also includes components for measuring the driving current that interact with an adjustable current-limiting device, thus allowing the pumping pressure of the pump to be adjusted and limited. The pump may include several pump cylinders which are controlled by a position control circuit in such a way that the generated partial vacuum follows a predetermined time characteristic.

5 Claims, 3 Drawing Sheets

VACUUM LIMITING MEDICAL PUMP

This is a continuation-in-part of application Ser. No. 08/198,825, filed Feb. 18, 1994 now abandoned.

The subject matter of this invention concerns a pump for use in medical technology according to the precharacterizing portion of patent claim 1.

This type of pump includes all pumps which can be used in the field of medical technology. In particular, these are pumps with which specific bodily secretions can be pumped, such as breast pumps for pumping breast milk, or pumps with which a partial vacuum or an excess pressure necessary for a specific surgical intervention can be ensured, such as thorax pumps for thorax operations.

Breast pumps have been known for some time and are used whenever the mother is unable or unwilling to nurse the baby directly., such as in cases in which, for example, the sucking power of the newborn baby is inadequate, as a result of which the milk production may not be sufficiently stimulated, or even in cases in which the sucking power of the baby is adequate, but the mother may not be able to nurse her baby because of overly sensitive and vulnerable nipples. Many types of physical and psychological disorders can be alleviated or cured with the use of an effective breast pump. For this reason, breast pumps in many different designs are being widely used in private homes as well as in hospitals. Thus, hand pumps and electrically driven suction apparatuses are presently being used. It is obvious that, depending on the reason for the nursing inability on the part of the mother, one breast pump may be more suitable than another. For example, in cases in which there is a need for establishing a sucking rhythm and/or a certain sucking power, electrically driven breast pumps are indicated.

One type of electrically driven breast pump has been described, for example, in the European Patent Application EP-A-330,845. With this pump, it is possible to generate a partial vacuum between 100 mm Hg and 250 mm Hg with a pumping frequency of 50 to 60 cycles per minute. The partial vacuum generated as well as its characteristics as a function of time are determined by a specially designed rotary disk and cannot be changed by the user. In many cases, however, it is desirable to manually limit the partial vacuum that is generated by the device.

Thus, the German Patent Specification No. 3,820,211 describes a suction device for use in medical technology in which the partial vacuum at a specific moment in time is recorded by a pressure sensor and its electrical signal is used to limit the partial vacuum generated. For this purpose, it is proposed that either the sucking rhythm of the pump be interrupted as soon as a specific limiting value for the partial vacuum (which can be freely selected or definitely set) has been reached or that the air suction volume of a vacuum pump, the volumetric rate of flow of which can be changed, be limited as soon as this specific limiting value of the partial vacuum has been reached. Again, this device cannot be universally used, it is mechanically complicated (servo drive for the pump and circuit for additional valves) and requires a correct, i.e., precise, fitting of the suction cup.

During the surgical treatment of pneumothorax, a partial vacuum is generated in the cavity formed between the thoracic cage and the collapsed pulmonary lobe as a result of the injured pleura so that this pulmonary lobe can be reinflated. During this procedure, more or less air generally enters this cavity either from the lung or from the thoracic cavity, which causes the generated partial vacuum to collapse. In addition, due to the natural respiratory movement of the patient, the pressure conditions between the pleural membranes are not stable, which interferes with the healing process of the injured pleura. Therefore, to this day, the partial vacuum required in pneumathorax treatments is generated by means of communicating pressure-equalizing bottles.

It is therefore the objective of this invention to develop an electrically operated, cost-effective, and safe suction pump for use in medical technology which does not have the disadvantages of the conventionally known devices and especially one which makes it possible to individually set the pressure characteristics over time, for example, the sucking power and the sucking rhythm, and which operates safely without requiring a precise fit of the suction cup.

This problem is solved according to this invention by incorporating the characterizing features of patent claim 1 into the suction pump for use in medical technology that was mentioned in the introduction above. Further embodiments and special designs of the pump claimed by this invention will be described in the subordinate patent claims.

The suction pump according to this invention is fitted with a pump drive, the motional cycle of which is not continuous. According to this invention, the drive used is a drive which changes its motional direction as the frequency which can be adjusted changes. To control the mechanical movement of the drive, an electronic circuit is provided. This electronic circuit makes it possible to control the current intensity and especially the current direction or the phase shift of the driving current. Since the force required in the pump cylinder is proportionate to the generated partial vacuum and the force applied in turn is proportionate to the driving current, it is easily possible to limit the partial vacuum as desired and to regulate the characteristics of the generated partial vacuum as a function of time by controlling the driving current.

Thus, the electronic control circuit claimed by this invention has components, by means of which it is possible to measure the current required by the pump drive. This measured value is fed to a motor current limiter and is subsequently compared to the desired value of a set-point adjuster to limit the maximum partial vacuum. As soon as the measured value exceeds the desired value, the current for the pump drive is limited to this desired value.

It is obvious that electromagnets, linear adjusters, direct-current or alternating current motors, etc., may be used to drive the pump. The movement of the pump, which is to be generated by means of this drive, can be implemented without requiring any further inventive steps by means of a lever system, a spindle unit, or a similar system. Depending on the drive used, it necessary to determine the position of the drive element at any given moment in time so as to be able to define or set the length of the lift of the pump. Also, the circuit according to this invention provides for the clock generator to be designed in such a way that it can be adjusted. Thus, it is possible to control the time characteristic of the partial vacuum and the quantity output of the sucked air electronically, which ensures that any suction curve desired can be generated. In addition, properties of the drive that might lead to misleading results, such as friction and hysteresis, can be corrected and compensated for. The partial vacuum can be determined by measuring the force by means of suitable sensors, such as transverse beams with a wire strain gauge, and it can be subsequently processed in the control circuit.

Below, this invention will be discussed in greater detail based on the preferred practical examples below which will be explained on the basis of the attached drawings.

Figure 1:
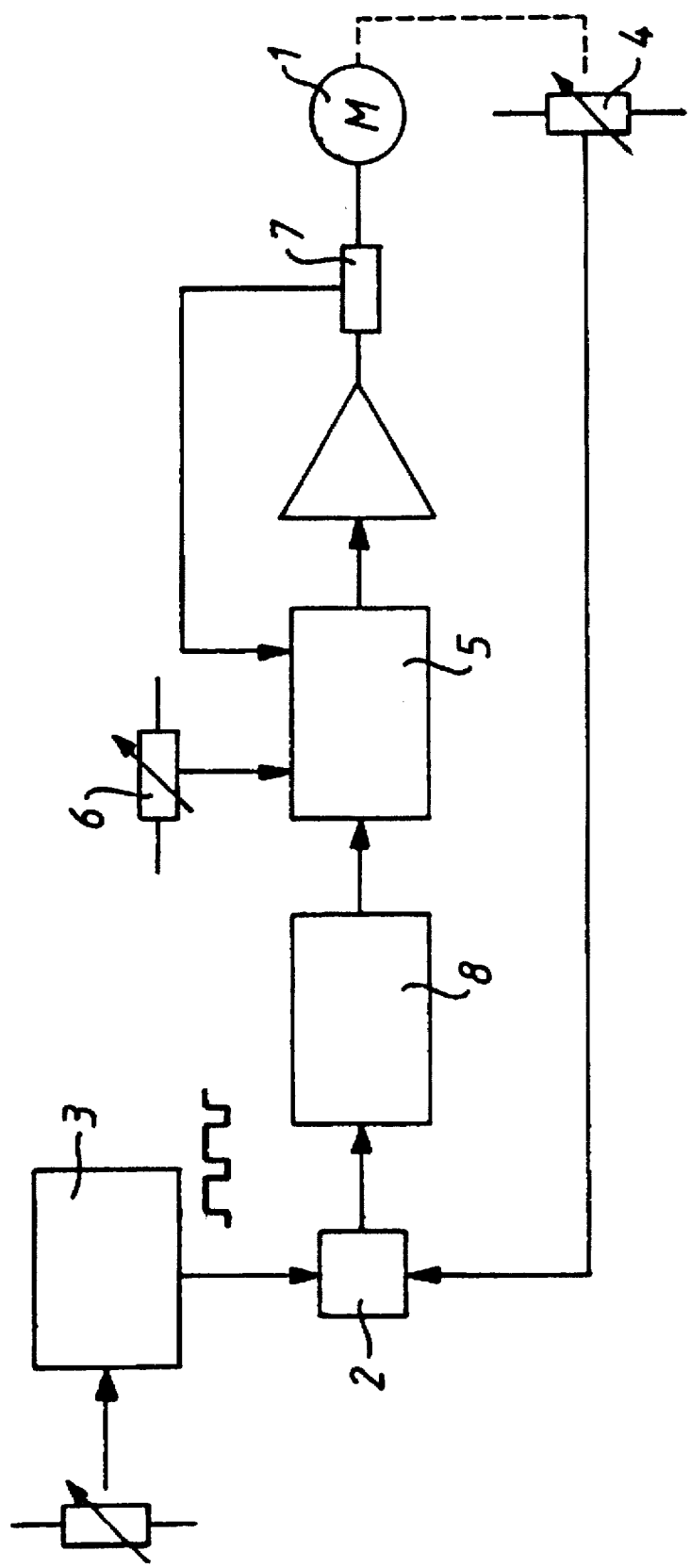
FIG. 1 shows a basic circuit diagram of the electronic control circuit according to this invention.

The basic circuit diagram that is depicted in FIG. 1 shows the electronic control circuit according to this invention for drive 1 of the pump cylinder unit. This drive may be designed, for example, in the form of an electric motor or an electromagnet. As provided by this invention, the current supply unit for this drive 1 has a comparator 2 which compares the desired value to the actual value. In a preferred practical example, this component 2 is controlled by an adjustable clock generator 3. It is obvious that the switching time for the transformation can be adjusted so as to coincide with the desired position of the pump cylinder unit. This adjustment can be set to a predetermined value; however, in an especially preferred practical example, it is implemented by an adjustable position detection device 4. This position detection device 4 determines the suction volume of the pump cylinder unit which is limited by means of a signal generated by component 4. In particular, this signal is fed to components 2, 8, and 5 to periodically transform the driving current or its phase shift.

To control the suction pressure of the pump, an adjustable current-limiting unit 5 is provided. According to this invention, this current-limiting unit 5 comprises a set-point adjuster 6, the signal of which is compared to an actual value signal which is generated by component 7 for measuring the driving current. The actual measured value of the driving current is directly proportionate to the direction of the rotation of the motor and thus to the suction pressure.

In a further development of the breast pump claimed in this invention, the pump cylinder unit comprises several pump cylinders which are suitably triggered by a position control circuit 8 to generate a uniform suction pressure. In particular, this invention provides for components which determine the position of the individual pump cylinders. When one of the pump cylinders reaches a preset final position, the position control circuit 8 activates the next pump cylinder. Thus, the position control unit 8 permits several pump cylinders to be triggered according to a predetermined pattern.

This position control circuit 8 also defines the point of reversal and, in particular, the zero position for each individual pump cylinder electronically. This is an especially important aspect of this invention since the pump volume of a breast pump, for example, may change during the pumping operation, which can lead to a hysteresis-like trend of the suction pressure. By scanning the actual value of the driving current, it is therefore possible to determine the actually applied partial vacuum or the presence of normal pressure in the pump cylinder regardless of the mechanical zero position.

When several pump cylinders are used, it is also possible to generate a predetermined holding pressure over an extended period of time, which is particularly important during thorax operations. In particular, the described position control circuit 8 makes it possible to maintain the desired partial vacuum even if a pump cylinder breaks down or if a partial vacuum system springs a leak, thus ensuring the high degree of operational safety that is a prerequisite of pumps that are used in medical technology. Similarly, the upper limit of the maximum suction pressure to be generated can be set by means of the pump according to this invention. In a further development of the pump according to this invention, this upper current limit is rhythmically varied over a predetermined time interval, for example, to stimulate the milk production.

Thus, the pump according to this invention makes it possible for the first time and at reasonable costs to individually adjust the properties of the pump by means of a simple arrangement, i.e., it makes it possible to freely select the pump volume, the pumping time, the pumping rhythm, and the pumping pressure and its characteristics as a function of time.

Figure 2A:
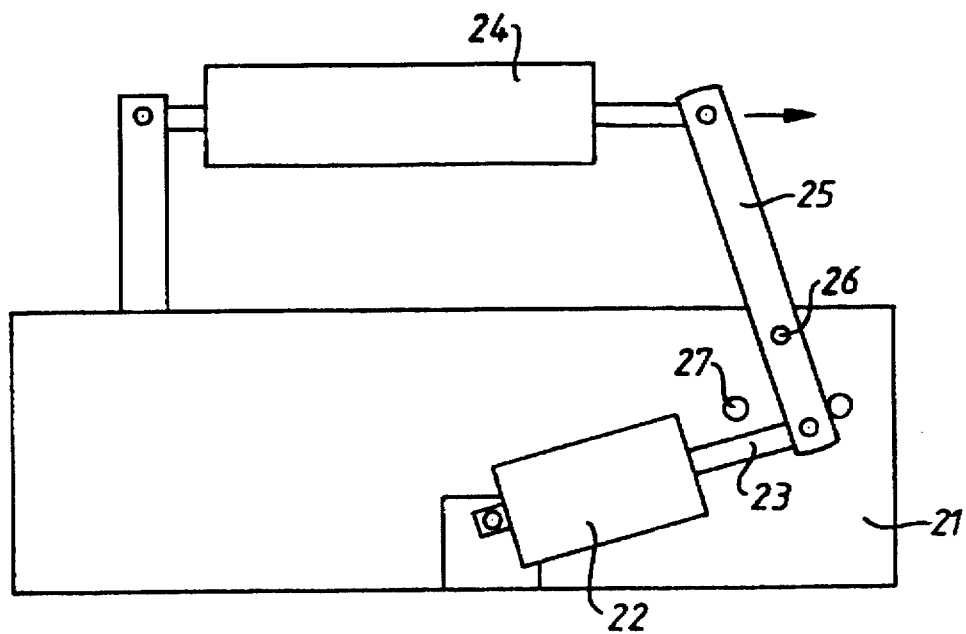
FIGS. 2a and 2b show preferred practical examples of the drive for the pump.
Figure 2B:
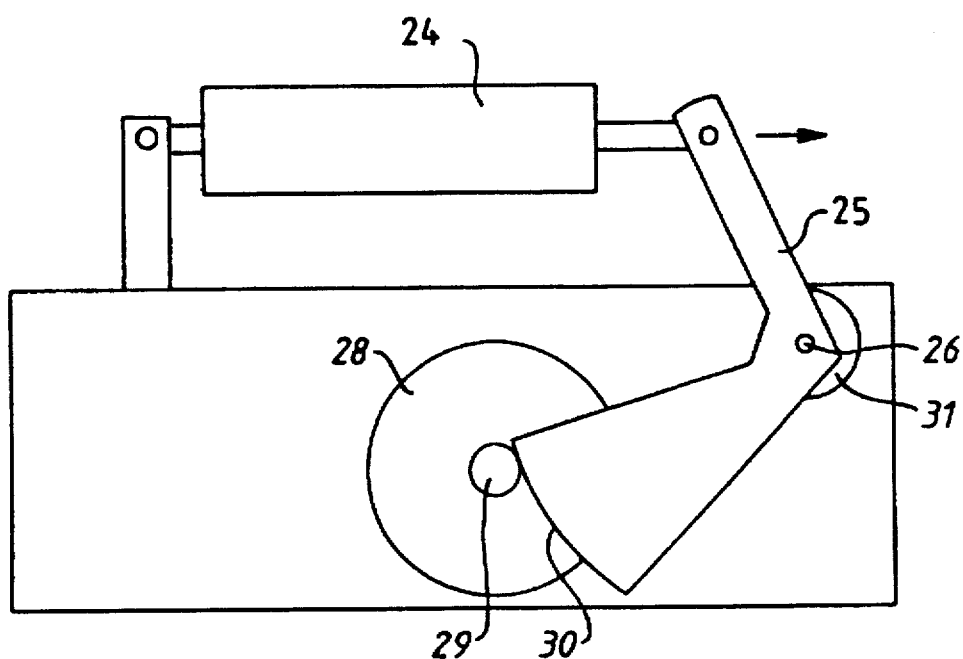

FIGS. 2a and 2b show the mechanical design of two embodiments of the pump as claimed in this invention. FIG. 2a shows a housing unit 21 in which at least one electromagnet 22 is located. The core 23 of this electromagnet 22 is connected to lever 25 which is linked to pump cylinder unit 24. This lever 25 swivels around a pivot 26 which is rigidly connected to the housing. A stop pin 27, the position of which can be set mechanically or electrically, limits the pump volume in a simple manner. The suction pressure desired is directly proportionate to the adjustable driving current of electromagnet 22.

The embodiment which is depicted in FIG. 2b shows an electric motor 28 with a current limiter which serves to limit the torque and which interacts with lever 25 via suitable gear teeth 29,30. This lever 25 is attached so as to be able to swivel around a pivot 26, which is rigidly connected to the housing, and drives the pump cylinder unit 24. A potentiometer 31 that is attached to pivot 26, which is rigidly connected to the housing, serves to detect the lever position and thus to determine the pumping volume.

Figure 3:
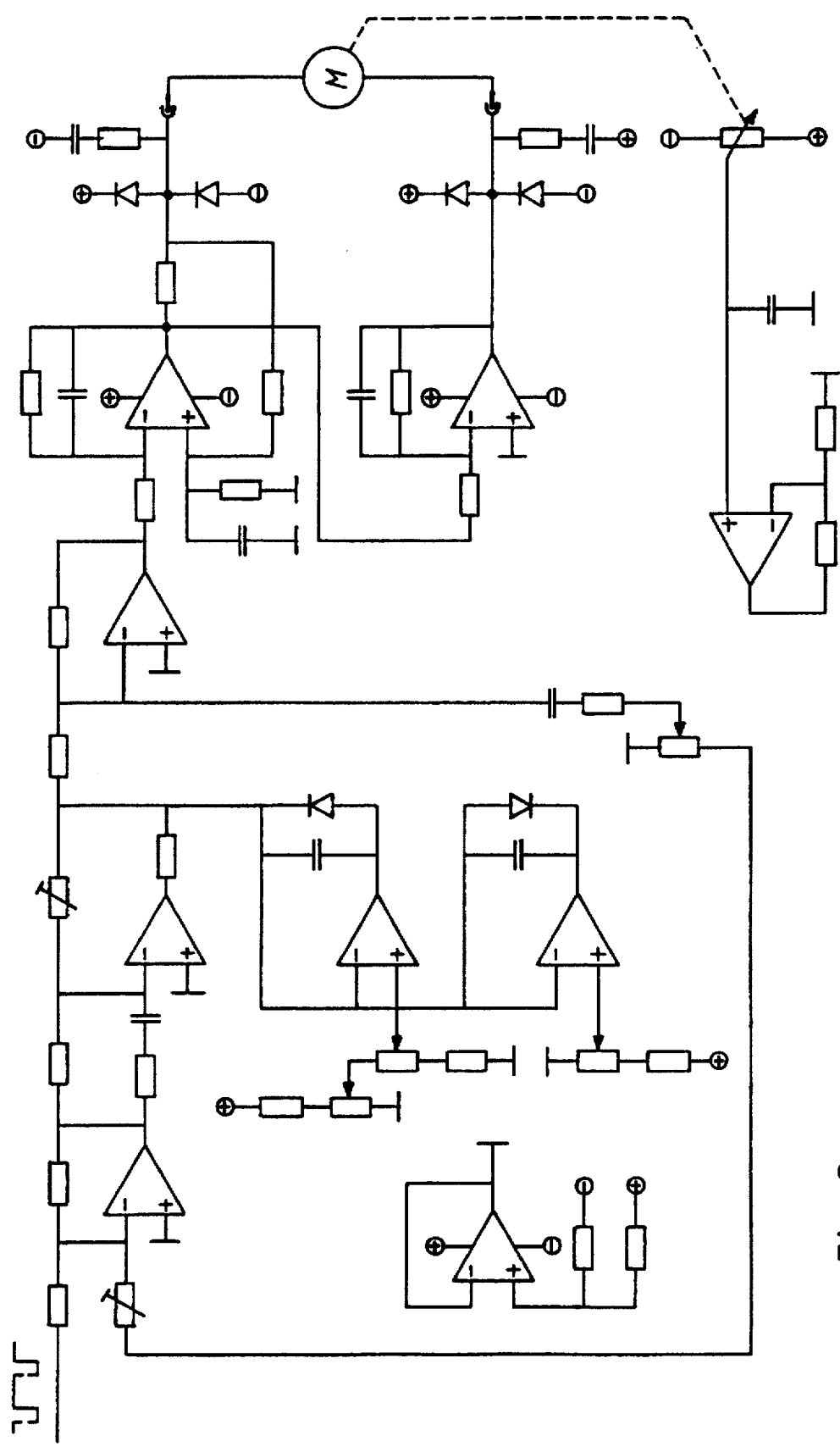
FIG. 3 shows a detailed circuit diagram of the electronic control circuit.

In the circuit diagram shown in FIG. 3, the electronic structure of an analog control circuit according to this invention is shown in detail and can be easily understood by those skilled in the art. Therefore, there is no need for further explanations.

The control circuit according to this invention may be either a printed analog circuit or a digital microprocessor circuit.

We claim:

1. Vacuum limiting medical pump comprising at least one pump cylinder unit (24), an electrical drive (1) for said unit, a current supply unit for generating a driving current for said drive (1), and an adjustable current-limiting device (5), and means (2,8,5) to periodically transform the driving current, said means to periodically transform the driving current including a controlled current set-point adjuster (2,5,8), and an adjustable clock generator (3).

2. The pump as claimed in claim 1, wherein means (7) is provided for measuring the driving current.

3. The pump as claimed in claim 2, wherein said means (7) for measuring the driving current are connected to said adjustable current-limiting device (5) for the drive (1) so as to be able to feed an electrical signal that is generated by said measuring means (7) as an actual value to said current-limiting device (5).

4. The pump as claimed in claim 3, wherein means (4) for detecting a mechanical position of the pump cylinder unit is provided which detects an electrical signal and which is connected to the means (2,5,8) to periodically transform the driving current.

5. The pump as claimed in claim 1, further comprising a microprocessor connected thereto for controlling the driving current.

* * * * *